(12) United States Patent
Dighton et al.

(10) Patent No.: US 9,647,289 B1
(45) Date of Patent: May 9, 2017

(54) UNIT FOR GLUCOSE DEPLETION

(71) Applicants: Haskell Dighton, Corsicana, TX (US); Patty Short, New Waverly, TX (US)

(72) Inventors: Haskell Dighton, Corsicana, TX (US); Patty Short, New Waverly, TX (US)

( * ) Notice: Subject to any disclaimer, the term of this patent is extended or adjusted under 35 U.S.C. 154(b) by 28 days.

(21) Appl. No.: 14/184,428

(22) Filed: Feb. 19, 2014

(51) Int. Cl.
| H01M 8/16 | (2006.01) |
| A61N 1/08 | (2006.01) |
| G01N 33/72 | (2006.01) |
| C12Q 1/25 | (2006.01) |

(52) U.S. Cl.
CPC ............... *H01M 8/16* (2013.01); *A61N 1/08* (2013.01); *C12Q 1/25* (2013.01); *G01N 33/721* (2013.01); *Y02E 60/527* (2013.01)

(58) Field of Classification Search
CPC ......... C12Q 1/25; H01M 8/16; G01N 33/721; G01N 33/726; Y02E 60/527
See application file for complete search history.

(56) References Cited

U.S. PATENT DOCUMENTS

| 3,811,950 | A | * | 5/1974 | Avampato | H01M 8/16 429/163 |
| 4,820,399 | A | * | 4/1989 | Senda | C12Q 1/004 204/403.09 |
| 5,888,787 | A | * | 3/1999 | Chen | C12N 9/0061 435/147 |
| 6,294,281 | B1 | * | 9/2001 | Heller | H01M 8/16 429/2 |
| 6,500,571 | B2 | * | 12/2002 | Liberatore | H01M 8/16 429/2 |
| 7,368,190 | B2 | * | 5/2008 | Heller | C12Q 1/26 429/2 |
| 8,415,059 | B2 | * | 4/2013 | Minteer | C12N 11/04 429/401 |
| 8,637,194 | B2 | * | 1/2014 | Long | H01M 14/00 429/401 |
| 2013/0171675 | A1 | * | 7/2013 | Tsukamoto | G01N 21/8483 435/14 |

* cited by examiner

*Primary Examiner* — Andrew Gilbert
(74) *Attorney, Agent, or Firm* — Harvey Law, P.C.; Derrick W. Harvey

(57) ABSTRACT

The present invention relates to treating of multiple pathological conditions through controlled lowering of glucose levels in blood. The present invention further relates to devices capable of lowering glucose levels in blood by exposing blood to enzyme-treated pole.

7 Claims, 2 Drawing Sheets

UNIT FOR GLUCOSE DEPLETION

BACKGROUND OF THE INVENTION

1. Field of the Invention

The present invention relates to treating of multiple pathological conditions through controlled lowering of glucose levels in blood. The present invention further relates to devices capable of lowering glucose levels in blood by exposing blood to enzyme-treated poles.

2. Description of Related Art

Many people have pathologies that result from, or perhaps cause unstable blood sugar levels. For example, common treatment for diabetes involves daily injects of insulin, islet transplantation, and kidney or even pancreas transplantation in some instances.

Research has been conducted in the area of utilizing glucose in blood to generate low-levels of power. These areas of development do not address a solution for methods of lowering glucose in a patient's blood through internal or external means, in a controlled process fashioned to the patient's specific needs. There remains a need for a medical service that reduces a patient's glucose level while generating low levels of power. There further remains a need for controlling a procedure to tailor towards a patient's needs.

SUMMARY OF THE INVENTION

The present invention has an objective to provide a solution for patients with high glucose. A further objective of the present invention is to provide a novel device for lowering the glucose levels in blood of a patient either externally or internally. Yet another objective is to enable the treatment by using electrical resistance and breaks within a circuit of the device. An even further objective of the invention is to produce low levels of power during the treatment process.

These and other objects were met with the present invention, which relates in a first embodiment to a device capable of removing glucose from the blood of a patient.

The present invention relates to a device and system for lowering the glucose level in a patient's blood. In one embodiment, the system may be implanted in the body to treat the blood in situ of the patient. In another embodiment, the system may be utilized outside of the body of the patient. The system comprises a cavity. A first enzyme-treated pole and a second enzyme-treated pole are positioned in the cavity, the first and second poles acting to induce a glucose-depleting reaction within the blood of a patient resulting in a flow of electrons. The system comprises further a conductive element that communicates with the cavity to conduct a current of electron flow. The system further comprises an inhibiting element to inhibit the electron flow. The system even further comprises a control panel that communicates with the inhibiting element of conductive element, whereby control panel may comprise devices or interfaces that control the rate of glucose depletion.

The system may include an energy output for utilizing the low-current flow of electrons generated by the system, the output conducting the flow of electrons to another utility. The output may conduct the flow of electrons through an induction or wireless transmission.

The present invention relates in a second embodiment to a method of lowering the level of glucose from a patient's blood by catalyzing a glucose-depleting reaction:

(a) Exposing the blood to a first enzyme-treated pole,
(b) Exposing the blood to a second enzyme-treated pole and creating a glucose-depleting reaction in which the glucose in the blood breaks down into constituent elements including a flow of electrons,
(c) Capturing the flow of electrons into a circuit that communicates with a control panel,
(d) Controlling the flow of electrons within the circuit by an inhibiting element,
(e) Selecting the rate of controlling the flow of electrons on the control panel, whereas the step of selecting the rate may be accomplished remotely of the site of the glucose-depletion reaction.

BRIEF DESCRIPTION OF THE DRAWINGS

The invention will now be described in greater detail with reference to the drawings, wherein.

DETAILED DESCRIPTION OF THE INVENTION

Figure 1:
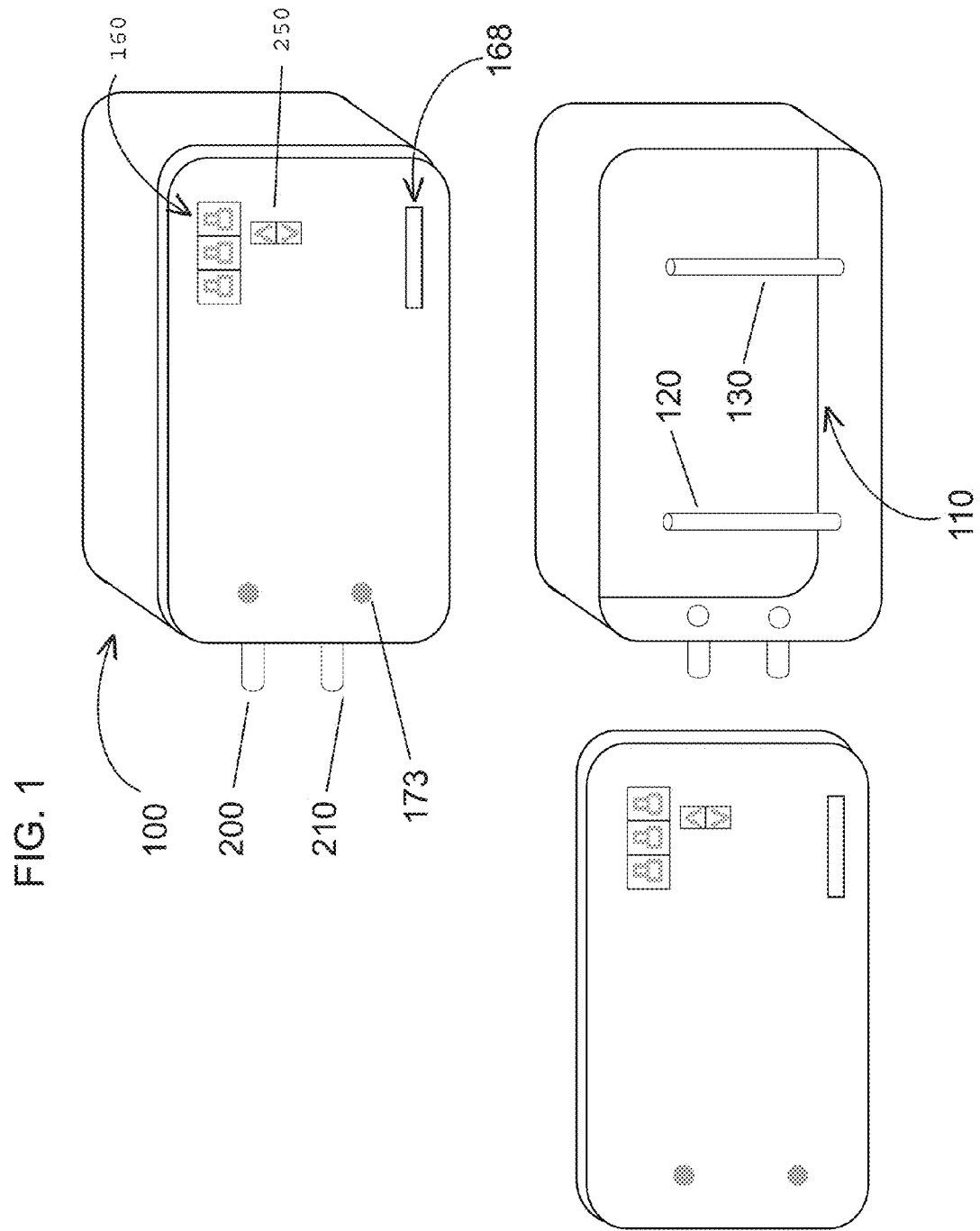
FIG. 1 depicts an embodiment of the device as an external unit.

Human blood has, at any given time, an ascertainable level of glucose. A medical patient who experiences levels of glucose that are higher than is desired during a course of treatment may seek treatment to lower the level of glucose. The presently-described invention lowers glucose by inducing a reaction within the blood of a patient seeking such treatment.

A patient's blood is exposed, in vitro or outside of the human body, to two enzyme treated poles, a first pole and a second pole. In one embodiment shown in FIG. 1, the first pole and second pole may comprise an anode and a cathode. The poles may have different structural configurations that the cylinder style shown in the FIG. 1. The enzymes used in treating the first pole and second pole are those known in the arts to catalyze the breakdown of glucose including amylases, sucrase, and lipase. One enzyme that may be utilized for this purpose is laccase. This may be desireable especially for the device to be implanted and utilized for the purpose of nanogeneration to create power for the inventive device as well as other devices used on or about a patient.

Together in the presence of a patient's blood products, the first pole and second pole catalyze glucose oxidation and oxygen reduction in an ensuing reaction without the need for external power. A naturally-occurring reaction takes place between the first and second enzyme-treated poles and causes the glucose to give up electrons that then flow toward the opposite pole through a control circuit. In other words, the reaction creates a current of low voltage. The control circuit may then convey the resulting current to an output for external use.

The present invention envisions a number of different embodiments of a device that would enable a user of the device to allow the above-described reaction to lower the concentration of glucose in blood. For the purposes of this specification, this reaction shall be referred to as glucose depletion. The reaction of glucose depletion causes the glucose in the blood to break down into its constituent elements, water and oxygen, and to no longer be identifiable as glucose.

The control circuit may be equipped with an inhibiting element to inhibit or break the flow of electrons and thus control the rate of glucose depletion. The inhibiting element applies a resistance to the control circuit to allow a controlled decrease in the glucose. The inhibiting element 180 may further comprise an inhibitor of variable resistance that may apply different levels of resistance as desired. Additionally, the control circuit 145 may be equipped with a break that selectively severs the flow of electrons and thus stops natural reaction of glucose depletion between the poles. The construction and network map of the electrical circuit is similar to those known in the arts to provide a simple, closed loop circuit with attributes described herein.

The present invention may include a control panel 160 to control the resistance of the inhibiting element 180 and thus, the flow of electrons that result from the glucose depletion. The control panel 160 may do so by communicating with an inhibiting element within the control circuit 145 of the device. By inhibiting the flow of electrons, one may reduce the rate of glucose depletion itself.

During use, the low voltage current that is generated by glucose depletion may be directed to an output. Output may take the form of port 168, as with the case of a USB port. The output may interact with charging interfaces for consumer electronic devices. It may be directed to interact and charge a medical device such as a defibrillator, an insulin pump, a pacemaker, or other energy consuming devices through induction or other wired transfer of energy.

Referring to the drawings, a first embodiment of the medical device according to the present invention is depicted in FIG. 1. In this embodiment, blood is treated outside the human body in an external device 100 that comprises an inlet 200 for blood supply and an outlet 210 for blood return. The blood enters the device 100 through the inlet 200 and into a cavity of the device. In a preferred embodiment, the patient's natural blood pressure will propel the blood through the inlet 200 and out the outlet 210 of the device 100. In other embodiments, a mechanical or electronic pump may be used to create a flow of blood through the device 100, such as a metered pump whose pressure and resulting blood flow rate is set at the control panel 160. Other pumps may be utilized within the scope of the invention, including those known in the arts such as a return pump on an aperri machine or on dialysis equipment. An enzyme coated anode pole 120 and an enzyme coated cathode pole 130 are positioned with in the cavity in such a way as to optimize and catalyze a glucose depletion reaction.

According to preferred embodiments, one or more sensors may be deployed to read the present the glucose level of the patient's blood as it enters or exits the cavity. Sensor 173 may "read" the respective glucose levels of the patient blood at the inlet 200 and outlet 210 of device 100, for example. The sensor 173 may read an initial glucose level of the blood and communicates this to the control panel 160 of the device 100. In FIG. 1, the control panel 160 includes a display that can indicate and toggle between the present level of glucose in the blood product of a patient and the desired level of glucose. A user may select the display output by engaging a button shown in FIG. 1. The control panel 160 shows a variable resistance selector 250 for the user to select to a desired level. According to embodiment shown in FIG. 1, the control panel 160 further comprises at least one port 168 for power input and output as well as data transmission. Port 168 may comprise a USB styled connector, though other connections known in the arts to transmit power and data are well within the scope of this invention.

Figure 2:
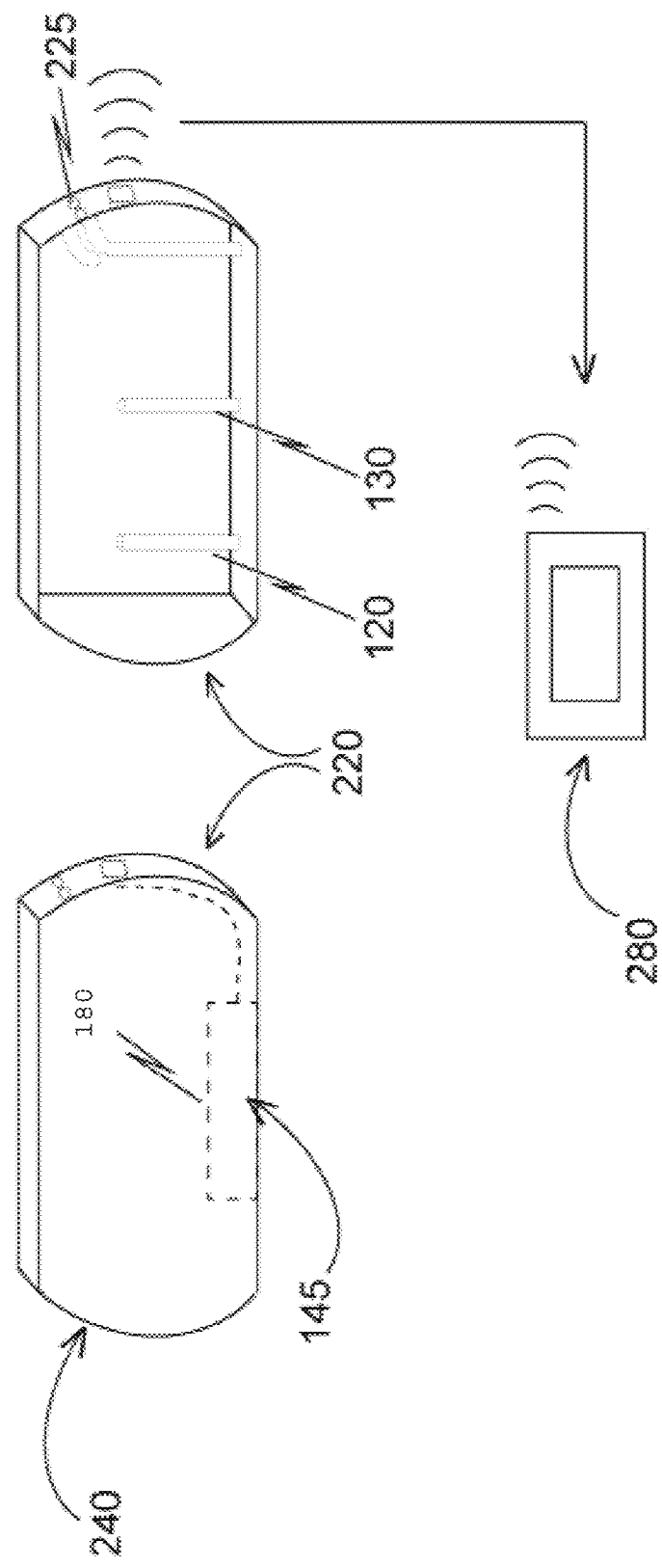
FIG. 2 depicts an embodiment of the device as an implant.

In another embodiment of the invention depicted in FIG. 2, an implant 220 for lowering glucose levels within the human body is disclosed. The implant 220 may comprise a set of enzyme coated poles, an anode and cathode connected by and comprising a control circuit. In FIG. 2 the circuit is built into the cover of the implant 220 though it may be positioned about other areas of the implant 220. The implant 220 may be positioned within many areas of the human body to interact with blood supply to catalyze glucose depletion. The implant 220 may be positioned within a blood vessel, within a cavity of the heart in a similar fashion as a pacemaker, or within the tissues that surround the spinal cord system.

In another embodiment of the invention, the implant 220 may comprise a cavity with an inlet and outlet in which to house the glucose depletion reaction. In still another embodiment of the implant 220, the rate of glucose depletion is controlled by a variable resistance, selected by a user of the implant 220 or a medical professional. A patient having the implant 220 may select the rate of glucose depletion based upon changes in the patient's biochemistry, the environment about the patient, level of activity of the patient, or other factors. In this embodiment, a wireless control panel 160 is utilized to control the rate of glucose depletion by selecting the desired level of variable resistance on wireless control circuit. Using the control panel 160, the patient may further program the inhibiting element to activate, change variable resistance, or completely "break" upon reaching a blood sugar level desired by the patient. The circuit may communicate to the panel through a communication port of the implant 220. The communication port may also wirelessly communicate with other medical devices used by the patient, including a heart defibrillator, a monitor, a pacemaker, or other non-medical devices such as a mobile computing device.

In another embodiment of the implant 220, the poles of the implant 220 may communicate directly with glucose in a blood supply, generating the glucose depletion reaction within the structures where blood naturally flows.

In yet another embodiment, the current that results from the glucose depletion reaction generated by implant 220 may be communicated through the communication port to an external system or device for use and/or consumption. For example, the current may be communicated to a pacemaker by induction or wireless transmission.

The present invention also embodies a method of treating blood products of a patient seeking a glucose-lowering treatment. The method may comprise the step of exposing blood products to a first enzyme-treated pole, exposing the blood to a second enzyme-treated pole and creating a glucose-depleting reaction in which the glucose in the blood breaks down into constituent elements including a flow of electrons, capturing the flow of electrons into a circuit that communicates with a control panel 160, controlling the flow of electrons within the circuit by an inhibiting element, selecting the rate of controlling the flow of electrons on the control panel 160, whereas the step of selecting the rate may be accomplished remotely of the site of the glucose-depletion reaction.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A device for treating multiple pathological conditions through controlled lowering of glucose levels in blood, the device comprising:
    a cavity comprising an inflow and outflow for blood products of the patient to be treated with the device to enter and exit the cavity, the cavity further comprising a first enzyme treated pole, the cavity further comprising a second enzyme treated pole of opposite polarity from the first pole, the first pole and second pole combining to break down glucose present in blood products of the patient into constituent elements including a flow of electrons, a control circuit connecting the first and second pole, a control panel capable of communicating with an inhibitor, the control panel comprising a selector for selecting a desired level of resistance to be applied to the control circuit, the control panel receiving an initial signal from a first sensor of an initial level of glucose in the patient, applying a rate of glucose depletion through the selection of the desired level of resistance for the selector to slow down the flow of electrons generated from the breakdown of glucose in the patient's blood products and thereby control the rate of glucose depletion of the patient's blood products, the control panel setting a desired level of glucose in the blood products of the patient, the control panel receiving a second signal from a second sensor of a level of glucose present in the blood products of the patient after the glucose depletion of the patient's blood products.

2. The device of claim 1, whereas the device is an external unit, the external unit comprising a display for selectively displaying a present level of glucose or a desired level of glucose.

3. The device of claim 1, whereby the device is an implant within the body of the patient.

4. The device of claim 1 further comprising an output for transmitting the flow of electrons.

5. The device of claim 4, whereby the output is a resistor.

6. The device of claim 1, whereby the enzyme in the first enzyme treated pole and the second enzyme treated pole is laccase.

7. A device for treating multiple pathological conditions through controlled lowering of a patient's glucose levels in blood products, the device comprising a cavity comprising an inflow and outflow for the blood products to enter and exit the cavity, the cavity further comprising a first enzyme treated pole, the cavity further comprising a second enzyme treated pole of opposite polarity from the first pole, the first pole and second pole combining to break down glucose present in blood products of the patient into constituent elements including a flow of electrons, an inhibitor for applying resistance to the flow of electrons that results from treating the patient's glucose levels, the inhibitor capable of slowing down the flow of electrons generated from the breakdown of glucose in the patient's blood products, a control panel communicating with the inhibitor, the control panel comprising a selector for manipulating a desired level of resistance to be applied to the flow of electrons the desired level of resistance being determined to balance the patient's blood sugar level, the control panel receiving a signal from a sensor to input an initial glucose level and a signal from the selector to select the desired level of resistance to set a desired glucose level, whereby the desired level of resistance lowers the patient's blood sugar level to the desired glucose level.

* * * * *